(12) United States Patent
Smith et al.

(10) Patent No.: US 7,556,733 B2
(45) Date of Patent: Jul. 7, 2009

(54) LOW VOLUME FILTRATION COLUMN DEVICES AND METHODS OF FILTERING THEREWITH

(75) Inventors: Thomas L. Smith, Campbell, CA (US); Derek S. Pai, San Francisco, CA (US); Steven T. Kunitake, San Carlos, CA (US); Derrick Richardson, Miramar, FL (US); Jorge Monteon, San Jose, CA (US)

(73) Assignee: MDS Analytical Technologies (US) Inc., Sunnyvale, CA (US)

( * ) Notice: Subject to any disclaimer, the term of this patent is extended or adjusted under 35 U.S.C. 154(b) by 290 days.

(21) Appl. No.: 11/076,272

(22) Filed: Mar. 9, 2005

(65) Prior Publication Data

US 2006/0037903 A1    Feb. 23, 2006

Related U.S. Application Data

(63) Continuation-in-part of application No. 10/209,508, filed on Jul. 30, 2002, which is a continuation-in-part of application No. 09/882,530, filed on Jun. 15, 2001, now Pat. No. 7,229,595.

(51) Int. Cl.
*B01D 29/00* (2006.01)

(52) U.S. Cl. .................................................. 210/240

(58) Field of Classification Search ............... None
See application file for complete search history.

(56) References Cited

U.S. PATENT DOCUMENTS

| | | | |
|---|---|---|---|
| 3,917,458 A | 11/1975 | Polak | |
| 4,214,993 A * | 7/1980 | Forsythe et al. | 210/282 |
| 4,320,769 A | 3/1982 | Eichhorn et al. | |
| 4,485,015 A | 11/1984 | Smith | |
| 4,520,716 A * | 6/1985 | Hayes | 99/306 |
| 4,683,058 A | 7/1987 | Lyman et al. | |
| 4,920,053 A | 4/1990 | Inoue et al. | |
| 4,957,624 A * | 9/1990 | Peranio | 210/129 |
| 5,057,426 A | 10/1991 | Henco et al. | |
| 5,075,430 A | 12/1991 | Little | |
| 5,103,338 A | 4/1992 | Crowley et al. | |
| 5,192,503 A | 3/1993 | McGrath et al. | |
| 5,234,809 A | 8/1993 | Boom et al. | |
| 5,246,866 A | 9/1993 | Nasu et al. | |
| 5,280,384 A | 1/1994 | Shibasaki | |
| 5,438,128 A | 8/1995 | Nieuwkerk et al. | |
| 5,494,646 A | 2/1996 | Seymour | |
| 5,496,523 A | 3/1996 | Gazit et al. | |
| 5,504,366 A | 4/1996 | Weiss et al. | |
| 5,513,768 A | 5/1996 | Smith | |
| 5,532,128 A | 7/1996 | Eggers et al. | |
| 5,538,849 A | 7/1996 | Uematsu et al. | |
| 5,545,531 A | 8/1996 | Rava et al. | |
| 5,559,329 A | 9/1996 | Joseph et al. | |
| 5,619,035 A | 4/1997 | Weiss et al. | |
| 5,639,428 A | 6/1997 | Cottingham | |
| 5,652,141 A | 7/1997 | Henco et al. | |
| 5,677,197 A | 10/1997 | Gordon et al. | |
| 5,722,553 A | 3/1998 | Hovatter | |
| 5,756,049 A | 5/1998 | Brayton | |
| 5,798,215 A | 8/1998 | Cathey et al. | |
| 5,808,041 A | 9/1998 | Padhye et al. | |
| 5,843,644 A | 12/1998 | Liotta et al. | |
| 5,843,767 A | 12/1998 | Beattle | |
| 5,859,699 A | 1/1999 | Baer et al. | |
| 5,860,937 A | 1/1999 | Cohen | |
| 5,874,219 A | 2/1999 | Rava et al. | |
| 5,879,625 A | 3/1999 | Roslaniec et al. | |
| 5,891,630 A | 4/1999 | Eggers et al. | |
| 5,910,246 A | 6/1999 | Walter et al. | |
| 5,985,085 A | 11/1999 | Baer et al. | |
| 6,020,186 A | 2/2000 | Henco et al. | |
| 6,103,195 A | 8/2000 | Shukla et al. | |
| 6,157,446 A | 12/2000 | Baer et al. | |

(Continued)

FOREIGN PATENT DOCUMENTS

| | | |
|---|---|---|
| WO | WO93/11221 | 6/1993 |
| WO | WO95/23960 | 9/1995 |
| WO | WO96/40435 | 12/1996 |
| WO | WO97/13838 | 4/1997 |
| WO | WO98/11989 | 3/1998 |
| WO | WO98/35215 | 8/1998 |
| WO | WO98/42874 | 10/1998 |
| WO | WO99/17094 | 1/1999 |

OTHER PUBLICATIONS

BIO-RAD, Life Science Research Products Catalog (1993), pp. 57 and 60-63 (BIO-RAD).*
U.S. Appl. No. 09/208,604, filed Dec. 8, 1998, Baer et al.
BIO-RAD Life Sciences Research Products Catalog (1993), pp. 57 and 60-63.
Bonner, R.F., et al. (1997) "Laser Capture Microdissection: Molecular Analysis of Tissue", Amer. Assoc. Advanc. of Sci., 278:1481-1843.

(Continued)

*Primary Examiner*—James O Wilson
*Assistant Examiner*—Jeffrey H Murray
(74) *Attorney, Agent, or Firm*—Fish & Richardson P.C.

(57) ABSTRACT

This relates to filter columns for isolating nucleic acids, particularly at small elution volumes. The filter column is adapted for stable placement within the upper portion of standard plastic collection tubes of various sizes. The body of the filter column has a number of surfaces to accommodate placement within variously sized collection tubes. The filter column contains nucleic acid-specific filter which can be located at alternate regions within the filter column, providing different filter surface areas and loading volume capacities using the same column body. The filter column has an opening on an upper end adapted to be sealed by a cap. A method for recovering nucleic acids using such filter column is also provided.

11 Claims, 13 Drawing Sheets

U.S. PATENT DOCUMENTS

| | | |
|---|---|---|
| 6,177,278 B1 | 1/2001 | Haj-Ahmad |
| 6,184,973 B1 | 2/2001 | Baer et al. |
| 6,204,030 B1 | 3/2001 | Liotta et al. |
| 6,215,550 B1 | 4/2001 | Baer et al. |
| 6,218,531 B1 | 4/2001 | Ekenberg |
| 6,277,648 B1 | 8/2001 | Colpan |
| 6,469,779 B2 | 10/2002 | Baer et al. |
| 6,512,576 B1 | 1/2003 | Baer et al. |
| 6,528,248 B2 | 3/2003 | Lossing et al. |
| 6,639,657 B2 | 10/2003 | Baer et al. |
| 6,697,149 B2 | 2/2004 | Baer et al. |
| 2001/0038449 A1 | 11/2001 | Baer et al. |
| 2002/0192656 A1 | 12/2002 | Richardson et al. |

OTHER PUBLICATIONS

Brignole, E. (2000). "Laser-Capture Microdissection," pp. 1-5, located at<<http://pubs.acs.org/subscribe/journals/mdd/vO3/109/html/toolbox.html>> from Modern Discovery, 3(9):60-70.

Chu, S. S. et al. (2000). "Laser Capture Microdissection: Applications in Cancer Research," Biomedical Products pp. 1-4.

Chiu, G. (1999). "The Ecosystems Within" Section F, Science & Technology San Jose Mercury News pp. 1-5.

Emmert-Buck, Michael R. et al., (1996) "Laser Capture Microdissection", Science, 274:998-1001.

Goldsworthy, S. M. et al. (1999). "Effects of Fixation of RNA Extraction and Amplification from Laser Capture Microdissection Tissue" Molecular Carcinogenesis 25:86-91.

Isenberg et al., (1976) "Cell surgery by laser micro-dissection: a preparative method." Journal of Microsopy, vol. 107, pt 1 pp. 19-24.

Meier-Ruge, W. et al., (1976) "The laser in the Lowry Technique for Microdissection of Freeze-dried Tissue Slices", Histochemical J., pp. 8:387-401.

Relman, (1999) "The Search for Unrecognized Pathogens," Microbes, Immunity, and Disease, www.sciencemag.org Science vol. 284, pp. 1308 1310.

Schindler, M., et al., (Jul. 1985) "Automated Analysis and Survival Selection of Anchorage-Dependent Cells Under Normal Growth Conditions", Cytometry 6:368-374.

Schindler, M. (Aug. 1998) "Select, Microdissect, and Eject", Nature Biotechnology 16:719-720.

Schutze, Karin & Lahr, Georgia (Aug. 1998) "Identification of Expressed Genes by Laser-Mediated Manipulation of Single Cells", Nature Biotechnology, 16:737-742.

Simone, N.L. et al. (1998). "Laser-Capture Microdissection: Opening the Microscopic Frontier to Molecular Analysis," Trends In Genetics 14(7): 272-276.

U.S. Appl. No. 09/121,635, filed Jul. 23, 1998, Baer et al.

U.S. Appl. No. 09/208,604, filed Dec. 8, 1998, Baer et al.

\* cited by examiner

LOW VOLUME FILTRATION COLUMN DEVICES AND METHODS OF FILTERING THEREWITH

CROSS-REFERENCE TO RELATED APPLICATIONS

This application is a continuation-in-part of U.S. Ser. No. 10/209,508, filed Jul. 30, 2002, which is a continuation-in-part of U.S. Ser. No. 09/882,530, filed Jun. 15, 2001, the entire contents of both of these patent applications are hereby incorporated herein by reference as if fully set forth herein.

BACKGROUND OF THE INVENTION

1. Field of the Invention

This invention relates to filtration filter columns and methods of filtering therewith. More specifically, this invention relates to system and methods for isolating nucleic acids such as ribonucleic acid (RNA) and deoxyribonucleic acid (DNA) from other materials such as enzymes, salts, buffers, small molecules, and cellular debris.

2. Discussion of the Related Art

Isolation and purification of nucleic acids play a central role in modern molecular biology, and increasingly in medicine. Both laboratory and diagnostic research require the use of nucleic acids in gene cloning and genetic analysis. Many of these techniques require keeping ribonucleic acid (RNA) or deoxyribonucleic acid (DNA) pure and free of contamination. In many instances, the availability of small amounts of starting sample material poses a problem during isolation of the nucleic acid. The limited amount of sample material makes the need to limit loss of the sample material a critical concern.

A known method for isolating nucleic acids from a small amount of starting material includes the use of a spin filter column ("filter column") that contains a nucleic acid binding material (i.e., a filter). Examples of binding material/filters include silicas like glass powder, silica particles, glass microfibers, diatomaceous earth, etc. These filters are often associated with a "filter surface area." This filter surface area is not limited to the surface area of a side of the filter. Instead, since the filters are usually comprised of microscopic fibers, particles, porous substances, etc., the filter surface area is actually defined by the surface area of the components, which comprise the filter. For example, a filter that comprises glass microfibers may have a filter surface area defined by the surface area of the microfibers within the filter (either all of the microfibers or a portion thereof).

In some cases, filter columns may isolate nucleic acids directly from cells or biological tissue. In the first step a filter column is inserted into a microcentrifuge tube (e.g., a 1.5 ml tube) and a solution containing nucleic acids along with undesirable impurities is loaded into the top of the filter column. Depending upon the application, the starting material containing the nucleic acids is prepared from cells that have been treated with a disrupting solution causing the release of the nucleic acids. Alternatively, the nucleic acid solution is the product of an earlier reaction step. In either case, the nucleic acid binds to the filter column filter in the presence of a chaotropic agent. Then the filter column is centrifuged in a microcentrifuge. Centrifugation forces the solution through the filter column's filter and binds the nucleic acid to the filter. Next, the filter with the nucleic acids bound therein is washed by applying a washing solution to the top of the filter column and centrifuging again. After each wash the filter column can be removed from the collection tube so that the material in the collection tube may be removed. Finally, placement of an elution buffer (usually water having a specific pH) at the top of the column and applying centrifugation elutes the nucleic acid that is bound to the filter. Given the proper pH, the nucleic acid dissolves and elutes with the liquid into the collection tube. It is important to note that the volumes of the binding and wash solutions can be relatively large, thus necessitating the use of a larger (1.5-2.0 mL) tube. On the other hand, the volumes for elution are often smaller, making it desirable to have a smaller tube for the elution step. Eluting directly into a smaller tube allows one to proceed to the next reaction step in the small tube, rather than having to pipette out of the large tube. It is desirable to use a small tube in downstream processes. As discussed herein, use of a pipette is undesirable as it introduces the risk of loss of samples as well as contamination of the sample. Moreover, as described herein, there are additional benefits in keeping the sample solution in a smaller tube.

Several companies provide kits that include filter columns designed to use this technique for isolating nucleic acids. QIAGEN, Promega, and Boehringer Mannheim GmbH offer filter columns based on the above-described principle. However, existing filter columns cannot be used interchangeably with collection tubes of different sizes. Instead, these previously known filter columns only fit into a single size collection tube (e.g., a standard 1.5-2.0 mL microcentrifuge tube.)

This limitation presents a problem as many applications may benefit if a single filter column could be interchanged with collection tubes of multiple sizes. For example, given a small amount of nucleic acid in the starting material, it is best to elute the purified nucleic acid into a very small volume of fluid so that nucleic acid does not become too dilute in the fluid. Obviously, the resulting combination of elution buffer and nucleic acid will occupy a small volume. Many applications that require processing of nucleic acid may benefit when storing this small volume of material in a smaller sized collection tube. For instance, an application such as amplification of the purified DNA by polymerase chain reaction (PCR) requires placement of the nucleic acid into a thin-walled 0.5 mL or 0.2 mL microcentrifuge tube.

Accordingly, it may seem ideal to use a smaller filter column, which is specifically designed to fit a 0.5 mL or 0.2 mL microcentrifuge tube. However, a significant drawback is that these smaller filter columns limit the amount of wash and binding solution that can be passed through the column with each bind/wash. This limitation necessitates additional wash steps and increased handling of the filter column and microcentrifuge tube, thus presenting an undesirable increased risk of contamination. Also, as discussed above, the requirement of large volumes of binding and wash solutions often necessitate the use of a larger collection tubes (e.g., a 1.5-2.0 mL microcentrifuge tube.)

The remaining alternative is to use a filter column specifically designed to fit into a larger collection tube (e.g., a 1.5 mL-2.0 mL microcentrifuge tube.) While this alternative minimizes the additional wash steps and increased handling discussed above, the alternative presents additional problems. For instance, after purification, the nucleic acid solution must be eluted from the filter column into an appropriately sized 1.5 mL-2.0 mL microcentrifuge tube. As discussed above, many applications may benefit by storing the elution buffer and nucleic acid in a smaller sized microcentrifuge tube. Consequently, the elution buffer and nucleic acid must then be transferred (e.g., by aspiration) into a smaller (e.g. 0.5 mL) tube. Again, this extra transfer step introduces the undesirable potentials of contamination and loss of some of the nucleic acid.

The present invention involves the elution of purified nucleic acids into small volumes (generally less than 20 microliters). The filters of the filtration columns described are adapted to optimally function with small elution volumes by minimizing fluidic holdup during the purification and elution procedures, and by tailoring the filter characteristics.

In view of the above, there remains a need to use different-sized collection tubes with a single filter column. The ability to use different-sized collection tubes with a single filter column, particularly when dealing with small elution volumes, overcomes the problems associated with the existing art.

The invention described herein addresses the problems discussed above. Moreover, the invention described herein allows centrifugation from one filter column into at least two distinct sizes of collection tubes. The disclosed invention may be used with commercially available collection tubes

BRIEF SUMMARY OF THE INVENTION

According to one aspect of the invention, there is provided a filter column for isolating nucleic acids from a liquid sample. The filter column includes a body having a passageway extending therethrough. The body has a first end, a second end, an outer surface, an inner surface and a longitudinal axis. The outer surface has at least one bearing surface for seating on at least one collection tube. The inner surface has at least one angled surface located proximate or above the bearing surface. The angled surface forms an angle with the longitudinal axis that is less than approximately 90 degrees. A filter is disposed within the passageway.

According to another aspect of the invention, there is provided a filter column that includes a body having a passageway extending therethrough. The body has an outer surface, an inner surface and a longitudinal axis. A filter is disposed within the passageway and the filter has a perimeter. A retainer is disposed within the passageway above the filter. The retainer has an outer edge, an inner edge, and an upper surface that is beveled.

According to another aspect of the invention, there is provided a filter column that includes a body having a passageway extending therethrough. The body has an outer surface, an inner surface, and a longitudinal axis. A filter is supported within the passageway and the filter has a perimeter. At least a portion of the filter proximate to the perimeter is compressed relative to a portion of the filter that is inward from the perimeter.

According to another aspect of the invention, there is provided a filter column that includes a body having a passageway extending therethrough. The body has an outer surface, an inner surface, and a longitudinal axis. A filter is disposed within the passageway and the filter has a perimeter. At least a portion of the filter has a greater density relative to another portion of the filter.

According to another aspect of the invention, there is provided a filter column for isolating nucleic acids into solution of a preselected elution volume. The filter column includes a body having a passageway extending therethrough. The body of the filter column has a first end, a second end, an outer surface and an inner surface. At least one filter is disposed within the passageway. The filter has a wetting capacity that is approximately equal to the preselected elution volume.

According to another aspect of the invention, there is provided a filter column for isolating nucleic acids into solution of a preselected elution volume. The filter column includes a body having a passageway extending therethrough. The body of the filter column has a first end, a second end, an outer surface and an inner surface. At least one filter is disposed within the passageway. The filter has a wetting capacity that is less than the preselected elution volume.

According to yet another aspect of the invention, there is provided a method for isolating nucleic acid material. The method includes the step of providing a filter column that is comprised of a body having a passageway extending therethrough. The body has an outer surface and an inner surface. The filter column also includes at least one filter disposed within the passageway. The filter has a wetting capacity. The method also includes the step of providing a solution containing nucleic acid material. The solution containing nucleic acid is transferred to the filter of the filter column. The solution is transferred from the filter column. Elution buffer is added to the filter in an amount substantially equal to the wetting capacity of the filter. Nucleic acid is eluted from the filter column.

According to another aspect of the invention, there is provided a filter column for isolating nucleic acids into solution of a preselected elution volume. The filter column includes a body having a passageway extending therethrough. The body of the filter column has a first end, a second end, an outer surface and an inner surface. A filter is disposed within the passageway. The filter has a shape that defines a volume. The filter is configured such that the volume defined by the shape of the filter is substantially equal to the preselected elution volume.

According to yet another aspect of the invention, there is provided a method for isolating nucleic acid material. The method includes the step of providing a filter column that is comprised of a body having a passageway extending therethrough. The body has an outer surface and an inner surface. The filter column also includes a filter disposed within the passageway. The filter has a shape that defines a volume. The method also includes the step of providing a solution containing nucleic acid material. The solution containing nucleic acid is transferred to the filter. The solution is transferred from the filter column. Elution buffer is added to the filter in an amount substantially equal to the volume defined by the shape of the filter. Nucleic acid is eluted from the filter column.

According to yet another aspect of the invention, there is provided a method for isolating nucleic acid material. The method includes the step of providing a filter column that is comprised of a body having a passageway extending therethrough. The body has an outer surface and an inner surface. The filter column also includes a filter disposed within the passageway. The method also includes the step of providing a solution containing nucleic acid material. The filter column is located in fluid communication with a first collection vessel. The solution containing nucleic acid is transferred to the filter. The solution is transferred from the filter column at a first speed followed by a second speed wherein the first speed is slower than the second speed. Elution buffer is added to the filter. Nucleic acid is eluted from the filter column.

According to yet another aspect of the invention, there is provided a method for isolating nucleic acid material. The method includes the step of providing a filter column that is comprised of a body having a passageway extending therethrough. The body has an outer surface and an inner surface. The filter column also includes a filter disposed within the passageway. The method also includes the step of providing a solution containing nucleic acid material. The filter column is located in fluid communication with a first collection vessel. The solution containing nucleic acid is transferred to the filter of the filter column. The solution is transferred from the filter column. Elution buffer is added to the filter. Nucleic acid is eluted from the filter column at a first speed followed by a second speed wherein the first speed is slower than the second speed.

According to another aspect of the invention there is provided a filter column. The filter column includes a body having a passageway extending therethrough. The body has a first end, a second end, an outer surface, and an inner surface. The outer surface includes at least two bearing surfaces for seating the filter column on collection vessels of at least two different sizes. A filter is disposed within the passageway and the cross-sectional area of the passageway is substantially constant.

BRIEF DESCRIPTION OF THE DRAWINGS

A clear conception of the advantages and features constituting the invention, and of the components and operation of model systems provided with the invention, will become more readily apparent by referring to the exemplary, and therefore nonlimiting, embodiments illustrated in the drawings accompanying and forming a part of this specification, wherein like reference numerals (if they occur in more than one view) designate the same elements. Consequently, the claims are to be given the broadest interpretation that is consistent with the specification and the drawings. It should be noted that the features illustrated in the drawings are not necessarily drawn to scale.

DETAILED DESCRIPTION OF THE INVENTION

The following discussion of the variations of the invention and the reference to the attached drawings are for explanatory purposes and do not exhaustively represent the possible combinations and variations of the invention. Those skilled in the art will readily appreciate that many variations may be derived using the following description. The following examples are intended to convey certain principles of the invention. These examples are not intended to limit the scope of the claims to any particular example. It is understood that the claims are to be given their broadest reasonable interpretation in view of the description herein, any prior art, and the knowledge of those of ordinary skill in the field.

Figure 1A:
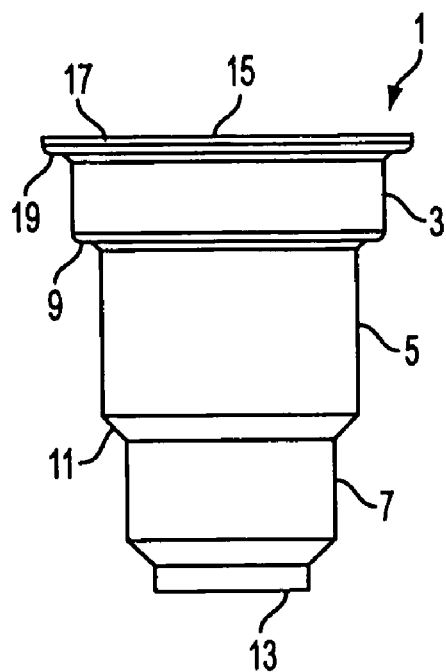
FIGS. 1A, 1B, 1C and 1D illustrate variations of filter columns of the present invention appropriate for mating with collection tubes of varying sizes.
Figure 1B:
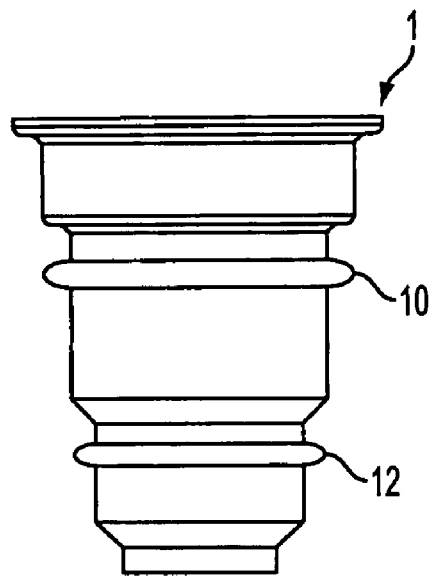

FIG. 1A shows a profile of a variation of the present invention. In this variation, the filter column 1 includes a passageway extending therethrough and a body portion that includes a first body portion 3, a second body portion 5, and a third body portion 7. The filter column 1 also contains a first bearing surface 9 and a second bearing surface 11 located between body portions 3, 5, and 7 as illustrated. The bearing surfaces are intended to permit placement of the filter column 1 in various collection vessels or tubes of at least two different sizes (e.g., see FIGS. 5 and 6). Accordingly, the present invention contemplates that the bearing surfaces, either alone, or along with body portion(s) adjacent to a bearing surface, serve to provide stability of a filter column when seated within a collection tube. Such stable placement is necessary for the intended use of the filter column (e.g., during centrifugation, vacuum filtering, handling, adding/removing material, etc.) Furthermore, although bearing surfaces 9, 11 are located at the intersection of the respective body portions, in other variations of the invention the bearing surfaces are located anywhere along the various body portions. As illustrated in FIG. 1B, the bearing surfaces 10, 12 are located along respective body portions of a filter column 1. Additionally, while bearing surfaces 9, 11, are illustrated as being tapered, the invention is not limited as such.

Variations of the invention also include filter columns with more than three body portions as well as filter columns with one or more bearing surfaces. The variation of the spin-column depicted in FIG. 1 further includes an outer rim 17 adjacent to a top 15 of the filter column 1. The outer rim 17 may also provide an additional bearing surface 19 and may also aid in grasping and manipulating the filter column 1. This rim is also used for mating with upstream devices that transfer solution to the invention such as an extraction device. The bottom of the filter column may be reduced in diameter 13 to assist in retaining a filter (not shown) within the filter column 1.

Figure 1C:
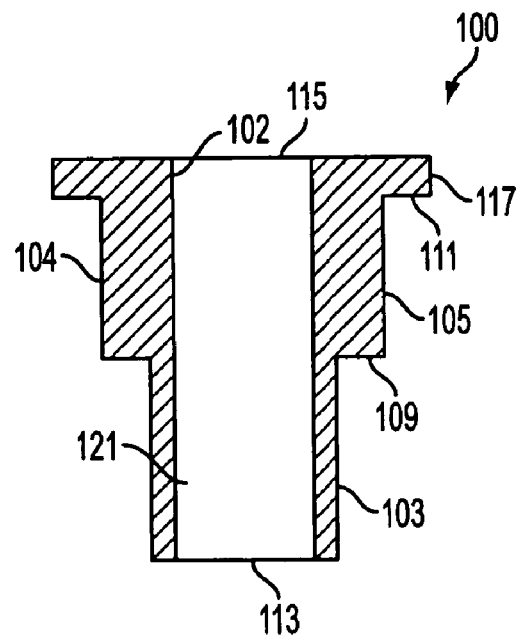
Figure 1D:
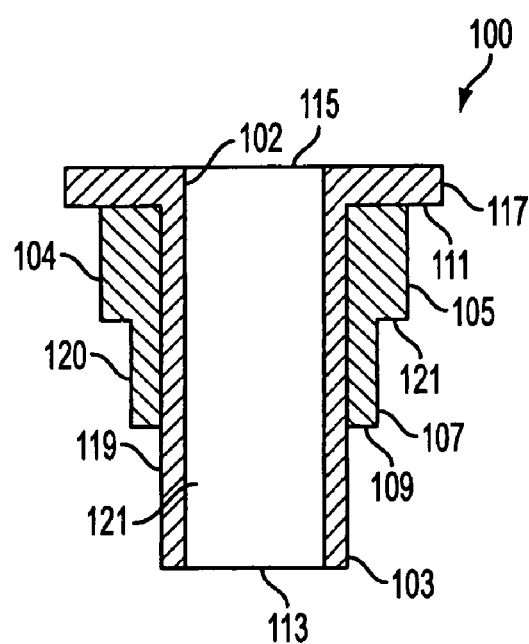

Another variation is shown in FIGS. 1C and 1D. The filter column 100 includes an inner surface 102 and an outer surface 104. A first body portion 103 and a second body portion 105 may also be defined. The filter column 100 includes at least one bearing surface 109 located between first body portion 103 and second body portion 105. A second bearing surface 111 is located between the second body portion 105 and a rim 117 adjacent to the top 115 of the filter column 100. As shown, the bearing surfaces 109 and 111 are formed in the outer surface 104. The inner surface 102 does not have any angled surfaces. The inner surface 104 forms a passageway 121 that extends throughout the length, from the bottom 113 to the top 115 of the filter column 100. The passageway 121 has a cross-sectional area that is substantially constant throughout the length of the passageway 121; however, the invention is not so limited. The inner passageway 121 may be tapered, include angled surfaces, and basically have a cross-sectional area that is not constant along the length of the passageway. As shown in FIG. 1C, the filter column 100 is formed in one piece.

FIG. 1D, illustrates a filter column 100 that is formed from two pieces-an inner portion 119 and an outer portion 120. The outer portion 120 may be separable form the inner portion 119 in one variation. Together, the inner portion 119 and the outer portion 120 provide an outer surface 104 that includes at least one bearing surface. At least two bearing surfaces are included such that the filter column is adapted to seat on collection vessels of at least two different sizes. The filter column 100 of FIG. 1D includes a first body portion 103, a second body portion 105 and a third body portion 107. The filter column 100 includes at least one bearing surface 109 located between the first body portion 103 and the third body portion 107. A second bearing surface 111 is located between the second body portion 105 and the rim 117 adjacent to the top 115 of the filter column 100. A third bearing surface 121 is located between the third body portion 107 and the second body portion 105. Of course, any number of body portions and/or bearing surfaces may be formed with the bearing surfaces being located anywhere along any body portion.

It is noted that the body of the filter column may be adapted as required to accommodate any particular filtration process for example, centrifugation, vacuum filtering, or any known filtering process. For example, if a filter column of the present invention is intended for use with vacuum filtering, the filter column may also include a manifold to accommodate the vacuum. Such modifications are well known to those familiar with filter columns and methods of using such devices.

The dimensions of the body portions 3, 5, 7, 103, 105, 107 are selected so that the filter column 1 may fit into various collection tubes that are sized for the respective body portion and bearing surface. Variations of the invention include sizing of a filter column to include body portions and bearing surfaces that accommodate both a 1.5-2.0 mL and a 0.5 mL microcentrifuge tube. An example of such tubes includes PGC Scientifics No. 16-8105-52 (1.5 mL) supplied by PGC Scientifics Corporation of Maryland, Eppendorf No. 22 36 430-8 (0.5 mL) supplied by Eppendorf AG of Germany, Gene Amp No. N801-0611 (0.5 mL) supplied by Perkin-Elmer Life Science of Massachusetts, Ciro Manufacturing Corporation of Pompano, Fla. (2.0 ml) and MJ Research, Inc. of Waltham, Mass. (0.5 ml). For example, the opening diameter for a 1.5 mL-2.0 mL microcentrifuge tube may range from 0.32-0.37 in. The opening diameter for a 0.5 mL microcentrifuge tube may range from 0.25-0.27 in. It is intended that, where appropriate, the definition of diameter of the filter column may include any such external feature as crush ribs, buttress, collar, or any other feature that may be present on a portion of a filter column body that is intended for insertion into a collection tube. The invention is not limited to filter columns or collection tubes having circular cross-sections.

While the invention may be suited for use with the tubes described above, the invention is not limited to compatibility with such tubes. Moreover, although variations of the inventive device described herein are discussed for use with existing microcentrifuge tubes ranging in size from 0.5 mL capacity to 1.5-1.5 mL capacity, the invention is not limited as such. Instead, the inventive device may be applied to collection tubes as described herein, centrifuge tubes of any size, or any type of collection tube where a benefit from the improvements of the current invention are desirable. Furthermore, the invention may be adapted to accommodate any number of combinations of large and small collection vessels, including, but not limited to a filter column adapted to accommodate a large 0.5 mL tube and a small 0.2 mL tube, or a filter column adapted to accommodate a large 1.5 mL tube and a small 0.2 mL tube.

The height of the filter columns of the present invention is selected so that the filter column along with the particular collection tube used will fit within the centrifuge apparatus (e.g., an Eppendorf 5415C centrifuge supplied by Eppendorf AG of Germany.) For example, for a 0.5 mL microcentrifuge tube to fit in the centrifuge previously listed, the height which protrudes from the 0.5 mL microcentrifuge tube (i.e., referring to FIG. 1A, the height from the top of bearing surface 11 to the top of the device) must be below 0.625 in. preferably below 0.5 in. Of course, height is not a constraint when used with vacuum filtering.

The filter columns of the present invention may be fabricated from materials readily known to those familiar with existing filter columns. Such materials include, but are not limited to polypropylene, polycarbonate, polyethylene, polyethylene terephthalate, fluoropolymers such as polytetrafluoroethylene and polyvinylidine flouride, polyarylene ether ketones, co-polymers and any thermoplastic or other commonly used material. It is often desirable to use a material, which is thermoplastic to allow molding of the columns. The columns can also be machined out of appropriate materials. In some cases, it is desirable to choose materials for the filter column, which permit sterilization and/or the removal of contaminants and harmful agents including the removal of nucleic acids and nucleases, thereby, allowing the filter column, filter, and sample to be nuclease-free.

Figure 2A:
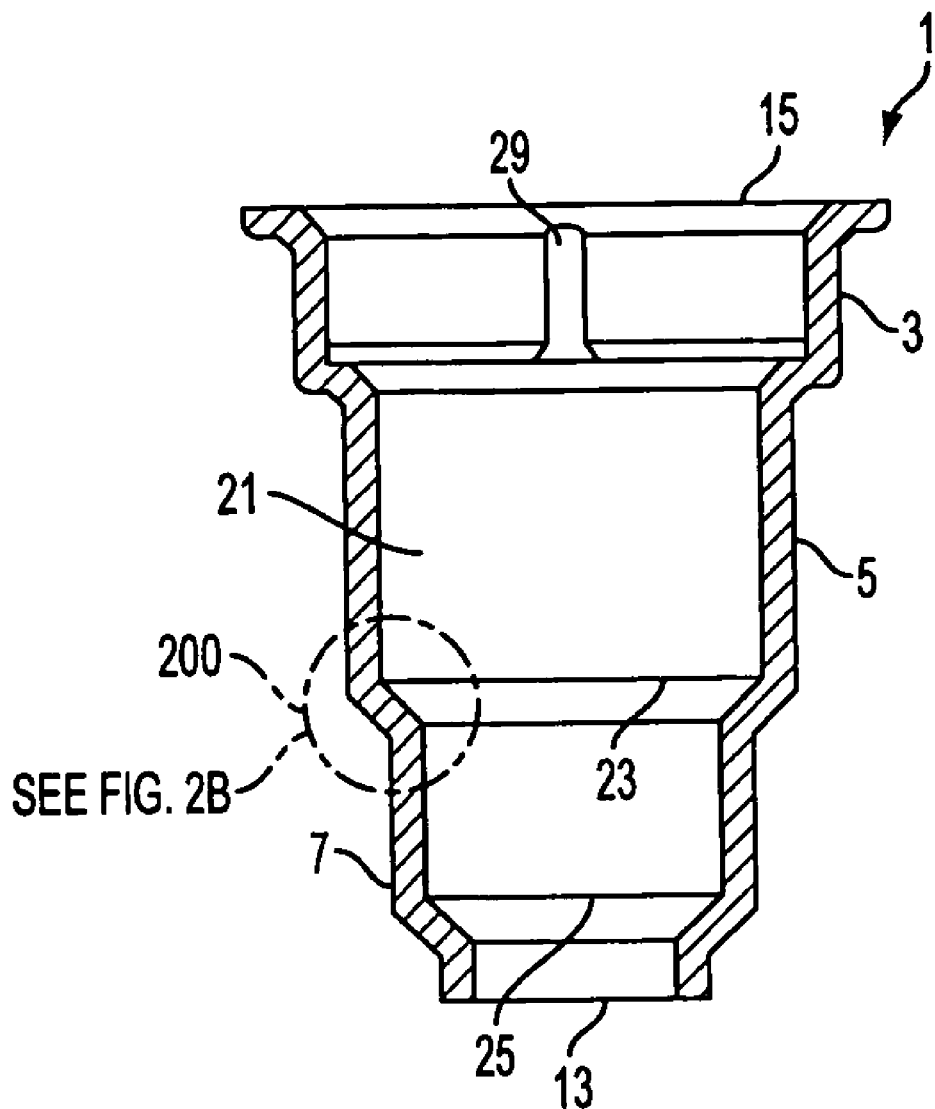
FIG. 2A illustrates a sectional view of a variation according to the invention.

FIG. 2 illustrates the internal body structure of a variation of a filter column of the present invention. In particular FIG. 2A, illustrates a cross-sectional view of a filter column 1 comprising a body having a passageway 21 extending therethrough. The body portion having an inner surface, an outer surface, a top end and a bottom end. In the variation shown in FIG. 2A, the filter column 1 includes a first body portion 3, a second body portion 5, and a third body portion 7. The body portions 3, 5, and 7 are interconnected in a telescoping fashion such that the width of the first body portion 3 is greater than the width of the second body portion 5 which is greater than the third body portion 7. As can be seen, body portions of different widths form bearing surfaces therebetween. The body portions together with the bearing surfaces enable the filter column to seat on collection vessels of different sizes. Still referencing FIG. 2A, for example, the filter column mates with a larger first collection vessel which seats against the bearing surface located between the first body portion 3 and the second body portion 5 such that the second body portion 5 is securely located inside the larger second collection vessel in a friction-fit engagement. A snap-fit engagement, or adhesive may also be employed to secure the filter column to the collection vessel. The filter column also mates with a smaller second collection vessel which seats against the bearing surface located between the second body portion 5 and the third body portion 7 such that the third body portion 7 is located inside the smaller first collection vessel in a friction-fit engagement. Of course, the filter column can mate with a relatively large collection vessel which seats against the bearing surface located between the rim and first body portion 3 such that the first body portion 3 is securely located inside the collection vessel. The filter column may be secured to the collection vessel using any means known to one skilled in the art. Also, in one variation, the cross-sectional area of the passageway 21 at the first body portion 3 is greater than the cross-sectional area of the second body portion 5 which is greater than the cross-sectional area of the third body portion 7.

Liquid solutions may be loaded into the top of the filter column 15 and a lid may also be used. Typically, liquid solutions include the nucleotide-containing solution, wash or rinsing solutions and an elution buffer (e.g. water or tris/ethylenediamine-tetra-acetate (TE)). The nucleic acid solution can be from a lysate (e.g. isolated directly from cells) or nucleic acids from a reaction mixture. The nucleic acids from reaction mixtures could be from reactions such as PCR, DNA or RNA polymerization, reverse transcription, etc. Before being loaded into the filter column the nucleic acid solution is usually combined with a binding buffer containing a chaotropic agent to aid in binding the nucleic acid to the filter. The compositions of binding buffers, wash or rinsing solutions and elution buffers are well known in the field and can be found in U.S. Pat. No. 5,075,430 to Little, U.S. Pat. No. 5,808,041 to Padhye, et al., and U.S. Pat. No. 5,652,141 to Henco, et al., the entirety of each is hereby incorporated by reference herein.

The variation of the invention depicted in FIG. 2A also illustrates a vent 29. The vent 29 may be located along an interior surface of a passageway 21 of a filter column 1 but will be placed in fluid communication with an exterior of the filter column 1. The vent 29 permits venting of pressure within the passageway 21 during placement of a lid (not shown) in the top opening 15 of the filter column 1. Without a vent, the placement of a lid could increase pressure within the passageway 21 such that sample material is forced out of the bottom 13 of the filter column 1. Although such displacement of the material may not have an effect on the function of a device of the present invention, such an occurrence may be undesirable. The device 1 may have any number of vents. These vents may be placed randomly or spaced evenly apart on a wall of a passageway. In one variation (not shown) four vents are placed at intervals of 90 degrees along the walls of the passageway. In another variation, a vent is placed in another location in the filter column 1 or even within a lid itself as described with respect to FIG. 12. In another variation, no vents are employed.

Figure 12:
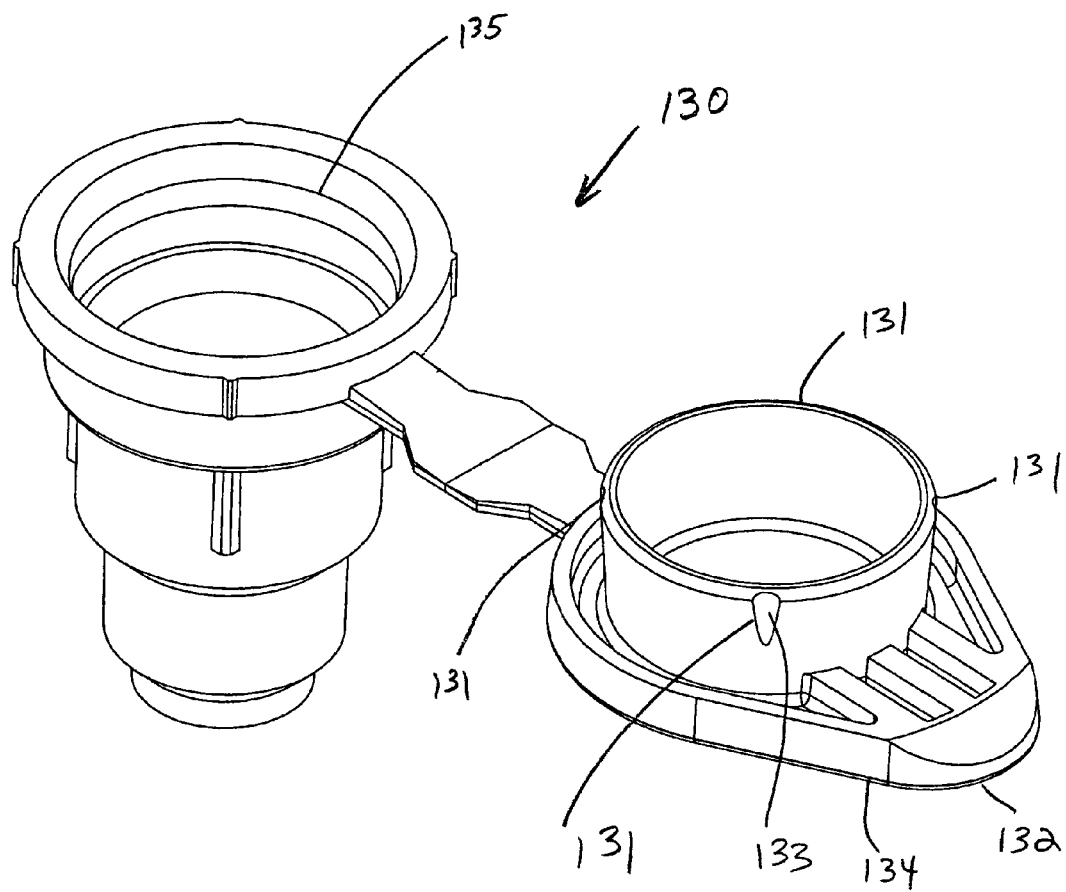
FIG. 12 illustrates a perspective view of the filter column of the present invention having vents located in the lid.

FIG. 12 illustrates a perspective view of a filter column 130 according to the present invention wherein one or more vents 131 are located in the lid 132. Vents 131 permit venting of air and prevent buffer, wash or elution fluid, for example, from being inadvertently pushed through the filter when the lid 132 is closed down onto the column. As shown in FIG. 12, the vent 131 has a curved surface 133. Also, the vent 131 is tapered such that the vent 131 is narrower towards the top 134 of the lid 132. These scalloped vents 131 that taper towards the top 134 of the lid 132 provide a more robust air and fluid barrier when the lid 132 is closed preventing fluid from spraying from, around, or through the lid 132. This variation allows no fluid to exit the column after the lid 132 closes with a snap-fit bead or ridge 135 located on the passageway of the column 130. Also, this variation makes manufacture of the filter column easier and less expensive because the injection molding tool does not have to accommodate a vent and a bead in the same location as required when the vent is formed in the passageway of the column. Therefore, the molding tool is easier to fabricate. Although four vents 131 are shown in the lid 132, the invention is not so limited and any number of vents 131 can be included in the lid. Similarly, the invention is not limited to scalloped or tapered vents.

Figure 2B:
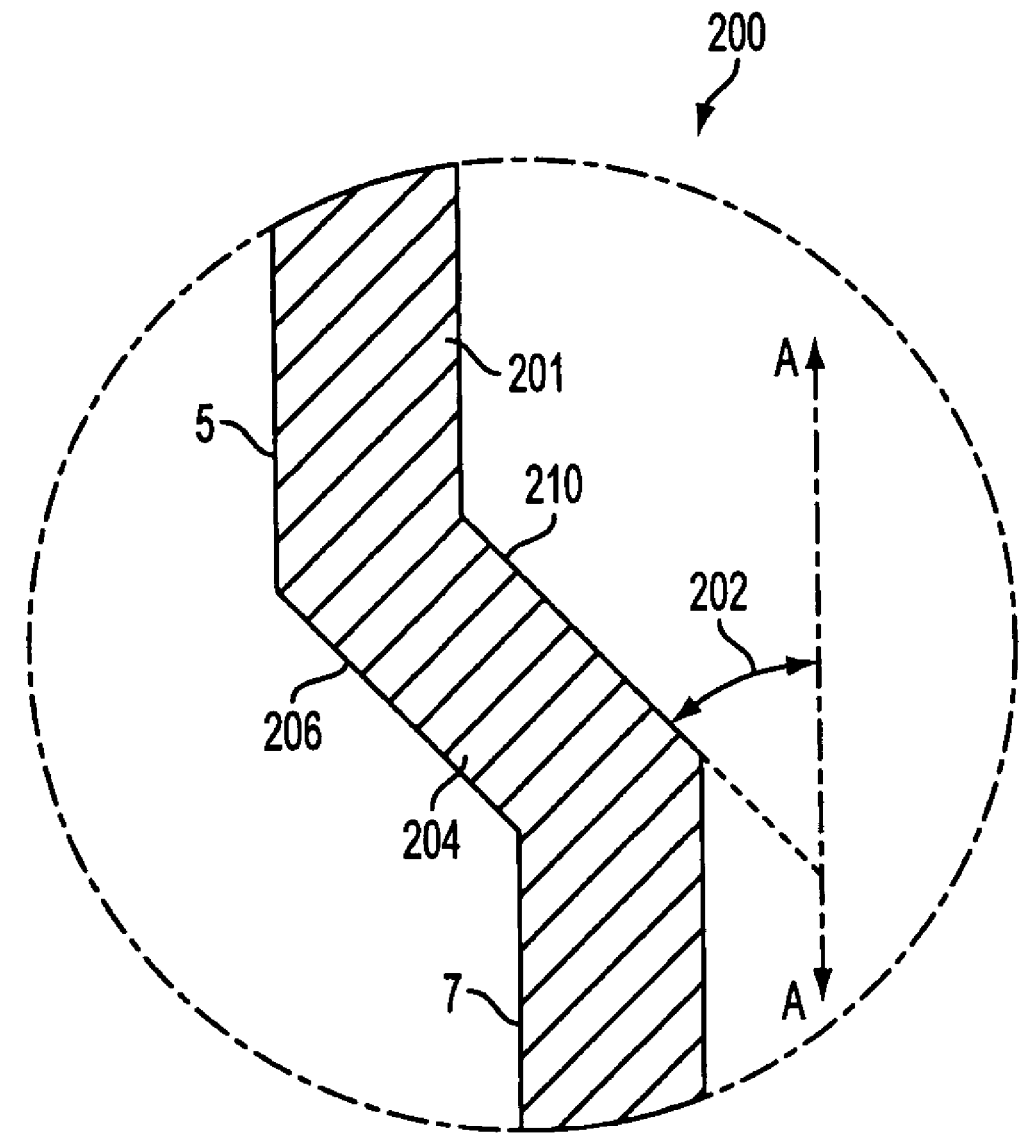
FIG. 2B illustrates a sectional view 200 of FIG. 2A.

FIG. 2B shows greater detail 200 of the juncture between two body portions. The wall 201 of the second body portion 5 connects to the wall of the third body portion 7 by an intermediary wall 204. The intermediary wall 204 has an outer surface 206 and an inner surface 210. The outer surface 206 of this intermediary wall 204 forms a bearing surface 11 as previously described. The inner surface 210 of this intermediary wall 204 is angled with respect to body portions 5 and 7 such that fluid in the filter column does not pool on the inner surface 210 while the filter column is in a stationary vertical position or while the filter column is undergoing centrifugation. An angled surface within the passageway need not be located at the intermediary wall. And, as shown above with respect to FIGS. 1C and 1D, an angled surface is not a necessary characteristic of the invention, as internal components, such as the filter and filter support, as well as external mating parts can be supported and/or retained by other methods such as with adhesive.

A funnel angle for the angled surface 210 is defined as the angle between the longitudinal axis A of the filter column and the angled surface 210 in question. The funnel angle of the angled surface is less than 90 degrees. In another variation, not only the juncture 200 of body portions 5 and 7 form a funnel angle that is less than 90 degrees, but also, the funnel angle of all junctures of the filter column passageway through which fluid must flow is less than 90 degrees whether or not the angled surface is located at the intermediary wall. This design advantageously prevents the creation of a shelf that is a potential source of fluid holdup when force is applied to the filter column. If the funnel angle of any angled surface is 90 degrees or more, fluid can be trapped on the angled surface. The funnel angle of a surface indicates whether fluid will collect on the surface. Fluid holdup should be avoided because it reduces the efficacy of the filter column purification. Thus, the inner passageway is designed to prevent fluid holdup within the filter column.

FIG. 2B shows the funnel angle 202 for the inner surface 210 when the direction of force applied is parallel to the wall 201 of the second body portion 5. As shown, the funnel angle 202 is approximately 45 degrees. This angle is less than 90 degrees required to prevent fluid holdup on this surface. FIG. 2B represents the case, of a filter column adapted for spinning in a microcentrifuge with a swinging-arm rotor so that the centrifugal force applied is substantially parallel to the walls of the second body portion. Alternatively, it would also apply if a vacuum or gravity were used to apply force to an upright filter column. Generally, the primary adaptation of the filter column is for it to be employed in a microcentrifuge with a rotor that holds the column at an angle of 45 degrees with respect to the direction of centrifugal force, and the depicted embodiment is designed for that case.

Preventing fluid holdup is particularly critical when eluting from the filter column into a small volume (e.g., less than 20 microliters). Many microcentrifuges have fixed-angle rotors where the tubes are held at a forty-five degree angle. In this example, the angle between the angled inner surface 210 and the wall 201 of the second body portion 5 is less than 45 degrees, resulting in a funnel angle that is less than 90 degrees. For other microcentrifuges that do not hold the tubes at 45 degrees, the surfaces of the passageway through the filter column could be designed so that the funnel angle remains less than 90 degrees throughout the passageway of the filter column. In another variation, the funnel angle 202 is approximately 30 degrees at one or more junctures.

As illustrated in FIG. 2A, the filter column 1 of the present invention also allows for varying placement of a filter (not shown) within a passageway 21 of the filter column 1. For example, placement of a filter in a bottom 23 of the second body portion 5 permits the filter column 1 to provide a certain volume capacity. The volume capacity of the filter column 1 can increase by changing the location of the filter to a bottom 25 of the third body portion 7. Accordingly, the same filter column 1 body may be used for varying application and more than one filter may be disposed within the filter column. To maximize the volume of fluid that can be added to a filter column of the present invention, a filter can be located in the lowest chamber. Moreover, locating the filter towards a middle chamber reduces the volume of fluid that may be added but permits a larger filter surface area as the diameter of the middle chamber may be greater than the diameter of a lower chamber. For the filter, it is desirable to have a high surface area glass fiber filter (e.g., a borosilicate glass). The filter may be one that is adapted to isolate nucleic acids from a liquid sample by, for example, centrifugation, vacuum filtering, or any other filtering method. Surface area refers to the total surface area of all the fibers and not just the area of the disk. Moreover, filter columns of the present invention may have a microliter capacity greater than 200 microliters. Another variation of the filter column having a microliter capacity ranging between 50 microliters and 1000 microliters. The microliter capacity is defined by the volume within a passageway of the filter column that is above the filter and not occupied by other components such as a lid.

The filter chosen can be silica or other types such as polymeric membranes, and may also contain other functional groups for purification of the nucleic acid such as ion exchange groups or groups which would specifically bind nucleic acid sequences. The structure and thickness of the filter will determine the filter wetting capacity. Wetting capacity is the amount of solution that can occupy the filter. For example, a filter made of glass fibers will have a wetting capacity approximately defined by the volume of space between the glass fibers. Thus, a rough approximation of the wetting capacity of a filter made of glass fiber could be determined by subtracting the volume of glass fiber from the total volume of the filter. The volume of the glass fiber can be determined by dividing the mass of the glass fiber filter by the specific gravity of the glass fiber. The wetting capacity can be determined by empirically measuring the amount of fluid a volume of filter material can hold. The wetting capacity is also called the void volume and other ways of measuring the void volume can be used to determine the wetting capacity. The quantitative definition of maximum wetting capacity is the void space within the filter. The void space within the filter can be calculated by taking the total space, both solid and void, that is circumscribed by the outermost fibers of the filter minus the solid space occupied by the filter fibers themselves. The space occupied by the filter fibers can be calculated by dividing the mass of the filter by the specific gravity of the fiber material. Other techniques known to one skilled in the art could also be used to determine wetting capacity and is within the scope of the present invention.

Wetting capacity can be used to optimize the dimensions of the filter used in the filter column, particularly for low-volume purification. A mismatch between the wetting volume and the volume of solution applied to the filter can decrease the yield of recovery of purification using a filter. For example, eluting purified nucleic acid into a preselected small volume (20 mL or less) of elution buffer when the wetting capacity of the filter is greater than the elution volume could result in incomplete recovery of the purified nucleic acid material. Thus, the elution buffer will not contact all parts of the filter that have bound nucleic acid, and therefore not all of the bound nucleic acid will be eluted. Additionally, if the elution volume is much larger than the wetting capacity, the effective in-filter residence time of the fluid is decreased from 100%, down to the ratio of wetted fluid to total volume. It is desirable to substantially match the wetting capacity of the filter chosen to the elution volume that is selected for the processes to be performed. To recover purified material into a low-volume of elution buffer (e.g., 20 microliters) using the inventive filter column, the filter has a similarly low wetting capacity. In one variation, the wetting capacity of the filter is substantially equal to the volume of elution buffer that is employed. A precise match between elution volume and wetting capacity is not required as long as it is plus or minus 10% of the elution volume. In one variation, the filter is configured such that the volume, that includes the space of both void and solid fiber as defined by the shape of the filter, is substantially equal to the preselected elution volume. In yet another variation, the wetting capacity is between approximately 8 microliters and 12 microliters.

In another variation, the wetting capacity is slightly less than the volume of elution buffer employed. In another variation the wetting capacity is approximately 66 percent to 100 percent of the elution volume. In another variation, the wetting capacity is approximately 50 percent to 100 percent of the elution volume. The wetting capacity of the filter column is easily modified by changing the dimensions of the filter, e.g. filter thickness, diameter, etc. If the filter is compressed, the wetting capacity is the resulting wetting capacity of the compressed filter.

At low volumes it may also be difficult to completely wet the filter because the surface tension may inhibit absorption into the filter. This is particularly critical when using low volumes of elution buffer. One solution is to include surface tension reducing agents, such as detergents, in the elution buffer. For example, addition of 0.1% of the detergent Triton X-100 could be included in the elution buffer to help wet the filter when eluting purified nucleic acid.

Securing of the filter may be accomplished, for example, by placement of a disk of porous substrate material (not shown) at approximately position 25 of FIG. 2A. A filter membrane (not shown) is placed on top of the substrate material. Optionally, a retainer (not shown) is added such that there is an interference or adhesion or interlocking between the retainer and the wall of the passageway. Accordingly, the retainer secures the filter on the porous substrate. Another means of securing the filter is to mold an integral grating within the passageway to seat the filter. FIG. 3C illustrates placement of a filter using the porous substrate and a retainer in the shape of a ring.

Figure 3A:
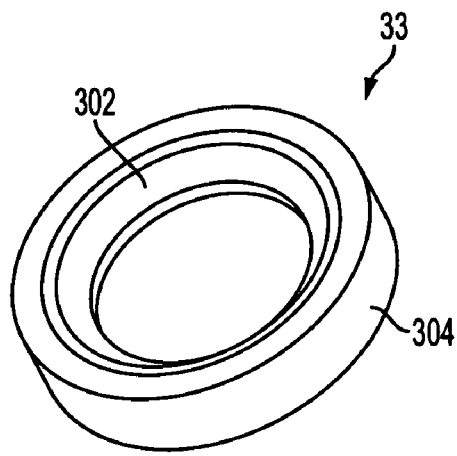
FIGS. 3A and 3B show perspective and cross-sectional views, respectively, of a variation of the retaining ring according to the invention.
Figure 3B:
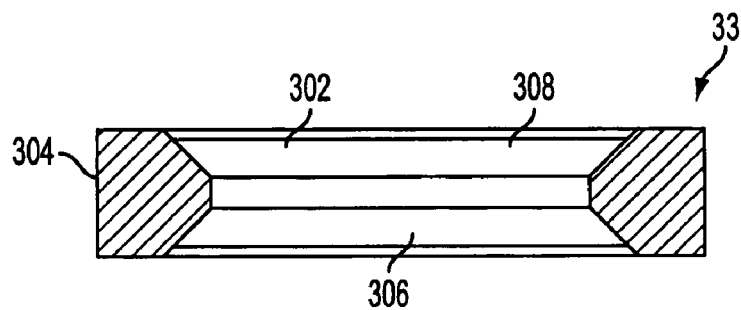
Figure 3C:
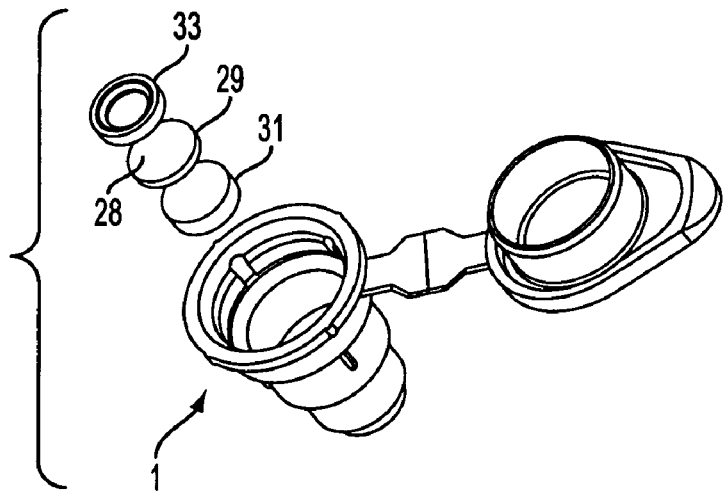
FIG. 3C shows an exploded view of the assembly of a filter, ring and support within the filter column of the invention.

FIG. 3A shows a perspective view of one embodiment of the retainer 33 of the present invention. The retainer 33 is shaped to substantially conform to the shape of the passageway. The retaining ring 33 includes an inner edge 302 and an outer edge 304. The inner edge 302 of the retaining ring 33 is beveled. This beveling creates a funnel angle that reduces fluid holdup. FIG. 3B shows a side cross-sectional view of the retaining ring 33 of FIG. 3A. The outer edge of the filter 304 is not beveled, and is designed to fit snugly against the walls of the passageway of the filter column. Alternately, the outer edge 304 may loosely fit and be attached to the inner wall of the passageway using an adhesive or other attachment means. As shown in FIG. 3B, the inner edge 302 includes a lower surface 306 and an upper surface 308. Both the lower 306 and upper 308 surfaces of the inner edge 302 of the retaining ring 33 are beveled in FIG. 3B such that the thickness of the retaining ring 33 decreases with distance from the outer edge towards the inner edge. The angle as well as the extent of this beveling can be varied resulting in a different funnel angle for the upper surface 308 of the retaining ring, or a different compression profile of the filter from the lower portion of the retaining ring. In one variation, the entire upper surface 308 of the retaining ring 33 is beveled, eliminating any shelf-like protrusion on which solution could collect while stationary or while undergoing centrifugation or vacuum filtering. The lower surface 306 may also have a similar beveled profile. In yet another variation, the funnel angle of the upper surface 308 is less than 90 degrees. Also, either one of the lower or upper surfaces may be beveled.

Figure 4:
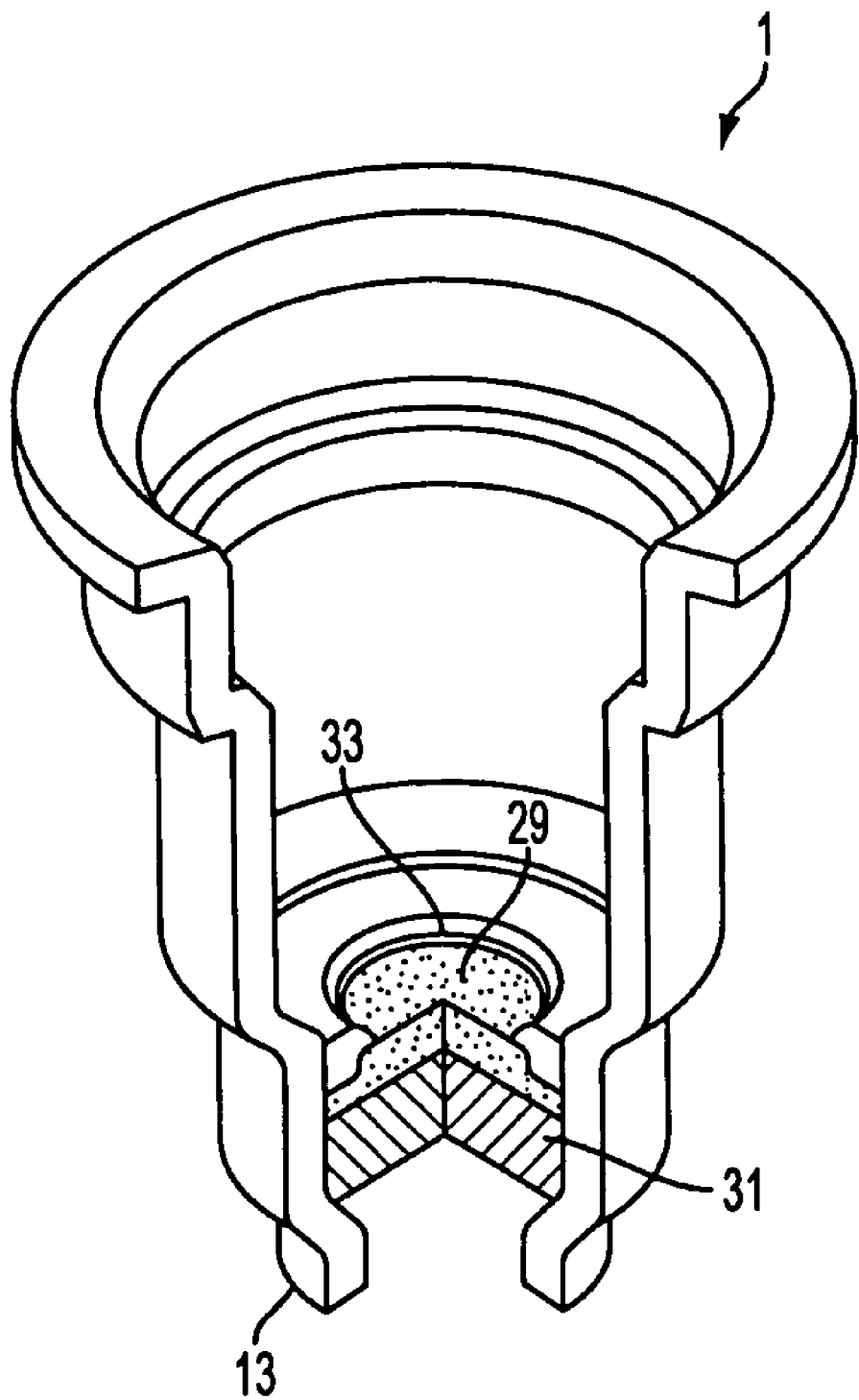
FIG. 4 illustrates a cut-away perspective view of a variation of a filter column of the present invention containing a filter, ring and support.

FIG. 3C shows how the retaining ring 33 inserts into the column filter in order to secure the filter in place. FIG. 3C illustrates an exploded view of a retaining ring 33, filter 29 and filter support 31 fitting into one embodiment of the filter column 1. The filter 29 is sandwiched between the retaining ring 33 and the filter support 31, and all three fit into the filter column. The filter support 31 and the retaining ring 33 match the diameter of the portion of the filter column into which they will be inserted. In one variation, when the retaining ring 33 is inserted, it abuts the filter 29 acting to compress at least a portion of the filter 29 that is proximate to the outer perimeter relative to a portion of the filter that is inward from the perimeter. In another variation, the insertion of the retainer 33 acts to increase the density of at least a portion of the filter relative to another portion of the filter. If a retainer 33 as shown in FIG. 3 is employed, the at least a portion of the filter of greater density is proximate to the perimeter of the filter relative to a portion of the filter that is inward from the perimeter. In one case, the top surface 28 of the filter 29 adopts a surface profile that is substantially complementary to the surface profile of the lower surface 306 of the retaining ring 33. A beveled lower surface 306 of the retaining ring 33 results in a gradient of compression across the filter 29 such that the middle region of the filter is uncompressed or only slightly compressed relative to the edge regions of the filter that are more compressed. The compression of the filter decreases the available surface area and wetting capacity in that region. While not bound by theory, this compression is believed to increase capillary affinity at the compressed circumference of the filter, and therefore, help draw fluid into the filter and toward the edges. A retainer need not be employed to compress at least a portion of the filter. FIG. 4 shows a filter column with the filter secured.

FIG. 4 illustrates a cut-away profile view of a variation of a filter column 1 of the present invention. The illustration shows a filter 29 held in the lower portion of the filter column 1. In this variation, the filter 29 is held between a porous support membrane 31, which has the same diameter as the interior of the lower portion of the spin column 1. In this variation, the support membrane 31 is retained in place by the shoulder formed by the reduced diameter of the bottom 13 of the device. The filter 29 may be fixed against the filter support membrane 31 by a retaining ring 33, which fits securely against the inner wall of the lower portion of the filter column 1. The present invention is not limited to the previous illustration. It will be apparent to those skilled with previously known filter columns to provide other means of retaining the filter within a filter column. An example of a filter for use with the invention includes a borosilicate glass fiber filter. The device may also contain filters of other types such as polymeric membranes, and may also contain other functional groups for purification of the nucleic acid such as ion exchange groups or groups which would specifically bind nucleic acid sequences.

The porous substrate could be comprised of a material such as a sintered polyethylene or polypropylene as supplied by Porex of Fairburn, Ga. or GenPore of Reading, Pa. In some variations of the invention it is desirable that the porous substrate is comprised of a hydrophobic material in order to minimize holdup of the aqueous solution and to prevent fluid intended for residence in the filter from exiting the filter prematurely. It was found that pore sizes in the range of 1 micron to 150 microns are useful. When the filter column is used for very low volumes of solution (e.g. elution buffer) it is preferred that the surface of the filter support that contacts the filter be substantially smooth and free from excessive pits or cavities. Although the filter support must be porous, gaps in the interface between the filter support and the filter create regions where fluid can leave the filter, reducing the amount of contact between the fluid and the filter fibers. Generally, it is better to have a more uniform and therefore more substantially smooth surface for the filter support. A smaller average pore size usually results in a more uniform filter support surface. The primary function of the porous material is support for the filter. It is also possible to have the porous support as integral to the device. The porous support can also be in the form of an open grating. It is also possible to have a filter that is strong enough to support itself or is materially combined with support material.

Figure 5A:
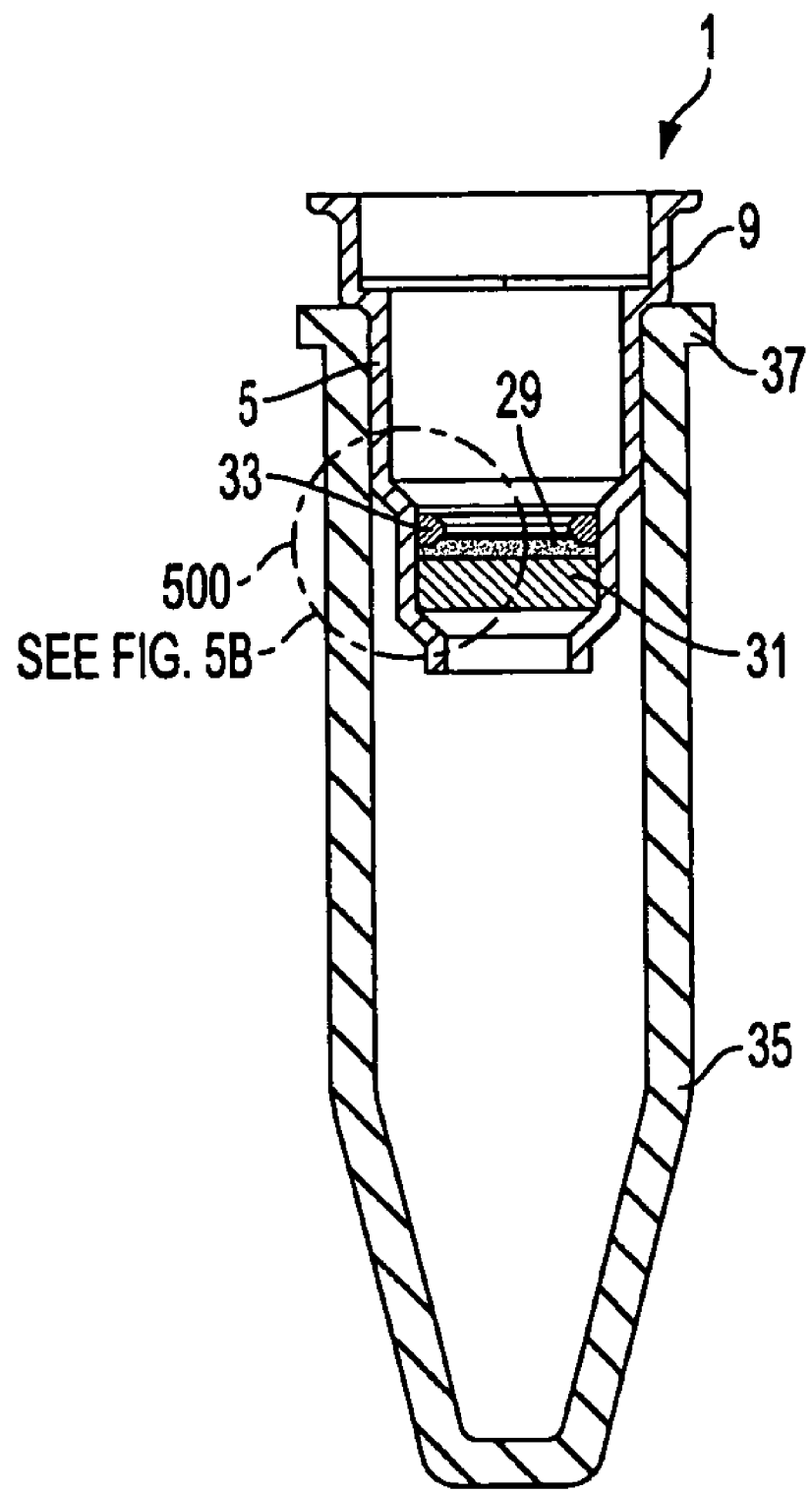
FIG. 5A illustrates a cross-sectional view of a filter column of the present invention removably seated in a first collection tube.

FIG. 5A illustrates a variation of a filter column 1 of the present invention that is mated with a standard collection tube 35 of a first size (e.g., a 1.5 mL tube.) Standard collection tubes contain an integral body made of polymers such as polypropylene and have a standard inner diameter. As shown in FIG. 5A, the second body portion 5 of the filter column 1 may fit securely against an inner wall of the collection tube 35. The first bearing surface 9 may rest against a shoulder formed by a rim 37 of the collection tube 35. Accordingly, when the tube 35 and filter column 1 spin in the centrifuge, liquid placed into the filter column 1 is forced through a filter 29 and collects in the collection tube 35. In this variation, the sizing of the first body portion 5 along with the bearing surface 9 permits stable placement of the filter column 1 within in the collection tube 35. After centrifugation, the filter column can be easily removed from the used collection tube, and placed into a new collection tube or placed back into the original tube.

Figure 5B:
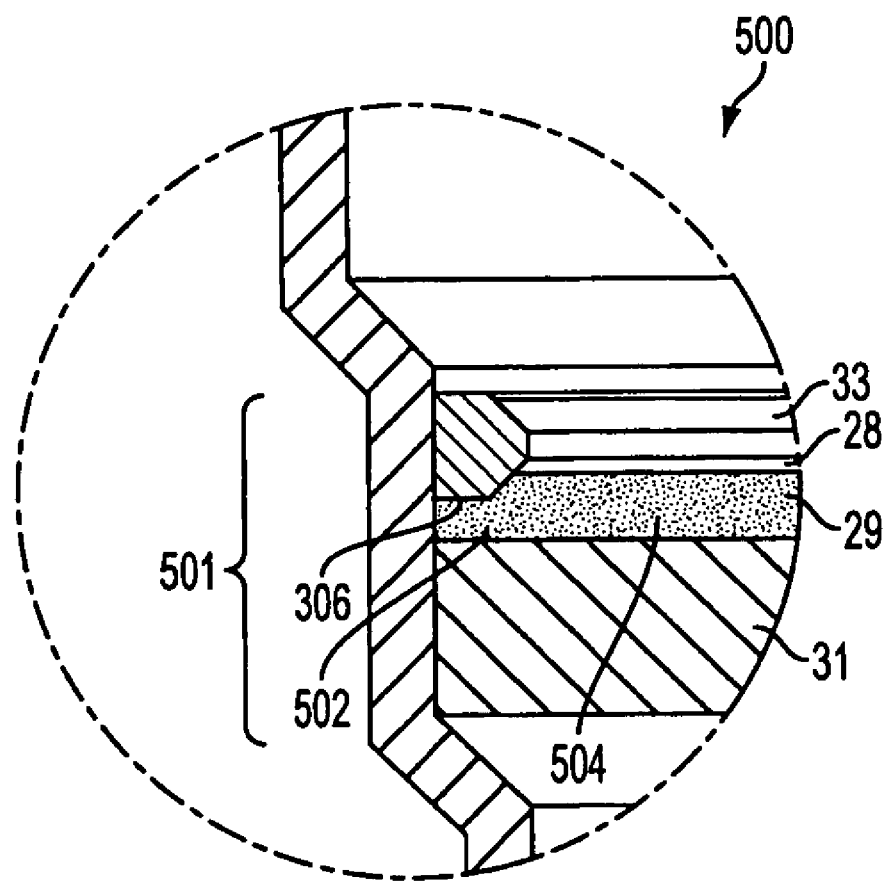
FIG. 5B illustrates a sectional view 500 of FIG. 5A.

FIG. 5B illustrates a view of section 500 of FIG. 5A. A retaining ring 33, filter 29 and a filter support 31 are disposed within a body portion 501 of the filter column 1. The body portion 501 has a volume. The filter 29 is located between the filter support 31 and the retaining ring 33. The top surface 28 of the filter conforms to the lower surface 306 of the retaining ring 33 such that the outer portion 502 of the filter 29 is more compressed relative to the inner portion 504 of the filter 29. As can be seen in FIG. 5B, the compression profile of the filter corresponds to the surface profile of the lower surface 306 of the retaining ring 33. In one variation, the filter has a compression profile such that the compression of the filter gradually increases with distance towards the outer edge. The compressed filter defines a volume. In one variation, the compressed wetting capacity of the filter 29 is selected to be approximately equal to or slightly greater than the elution volume.

Figure 6:
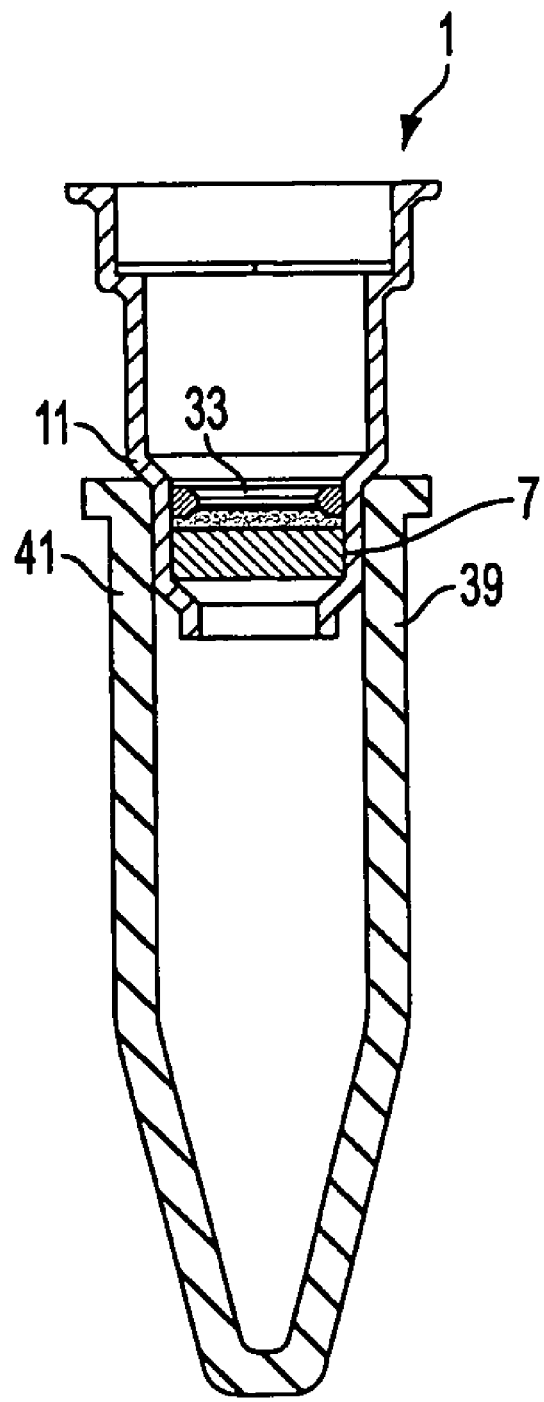
FIG. 6 illustrates a cross-sectional view of the filter column illustrated in FIG. 5 removably seated in a second collection tube being of a different size than the first collection tube of FIG. 5.

FIG. 6 illustrates the filter column 1 of FIG. 5 placed within a collection tube 39 (e.g., a 0.5 mL tube) that is smaller than the tube illustrated in FIG. 5. As illustrated in FIG. 6, the third body portion 7 of the filter column 1 fits securely into the inner walls of the collection tube 39. During centrifugation, a bearing surface 11 of the filter column 1 seats against a rim 41 of the collection tube 39.

Figure 7A:
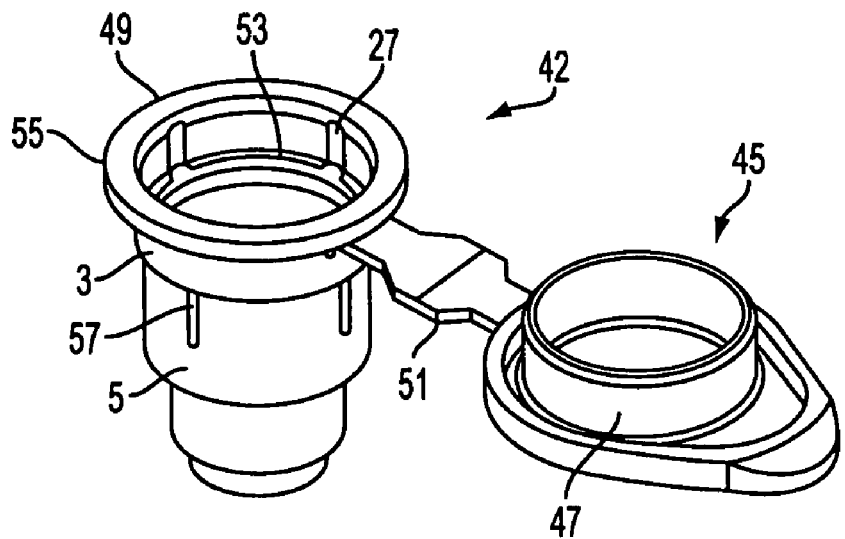
FIGS. 7A and 7B illustrate additional aspects of the invention that may be combined with any variation of the invention singly or in combination.

FIG. 7A shows another variation of a filter column 42 of the present invention having features, which may be applied to any variation of the invention disclosed herein. In this variation the filter column 42 includes a lid 45 having a portion 47 which may be removably secured within a first end 49 of the filter column 42. The lid 45 may assist in preventing contamination of the filter column 42 and any solutions loaded therein and may provide a surface for labeling. As shown, this variation of the filter column 42 contains a vent 27. Although this variation depicts the lid 45 as being integral with the filter column 42 via a hinge 51, the invention is not limited as such. For example, the present invention also includes a lid as being discrete from a filter column.

As illustrated in FIG. 7A, the variation of the inventive filter column also may include one or more snap-fit beads or ridges 53 to assist in retention of a lid 45. In this variation the ridge 53 is included in the in a portion of a passageway in a first body portion 3 of the filter column 42. As depicted in FIG. 7A, the lid 45 and hinge 51 may be attached to the underside of an outer rim 55 (e.g., subflush to the rim 55) of the filter column 42. This placement allows the outer rim 55 to be mated to other devices as required (e.g., a ExtracSure.™. sample extraction device useful for laser capture microdissection supplied by Arcturus Engineering of Mountain View, Calif. or other sample carrier).

Another aspect of the invention depicted in FIG. 7A is deformable ribs 57, which may be located along an outside surface of the filter column 42. The deformable ribs 57 assist in securing the filter column 42 in a slightly larger diameter tube (e.g., a 2.0 mL tube) by increasing a diameter of the filter column 42 for a friction-fit engagement, for example. Accordingly, these ribs deform upon insertion of the filter column 42 into a tube having a diameter slightly larger than the corresponding body portion upon which the ribs 57 are situated. The number and design of the deformation ribs 57 may vary as needed, however, the ribs should be placed on a portion of the filter column that accommodates the varying sizes of tubes. The invention also contemplates deformation ribs 57, which are either plastically or elastically deformable, or exhibit a limited degree of plastic or elastic deformation.

Figure 7B:
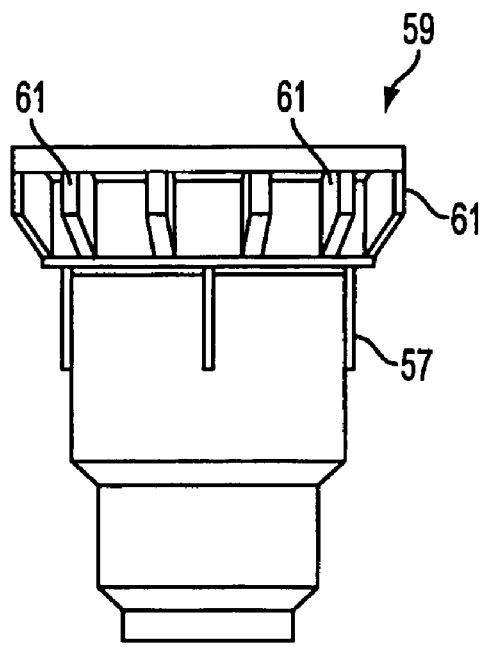

FIG. 7B illustrates another aspect of the invention, in which a filter column 59 contains at least one protrusion 61, which extends radially away from the filter column 59. Such protrusions 61 may serve as "finger grips" to increase the ease with which the filter column 59 may be manipulated.

Figure 8:
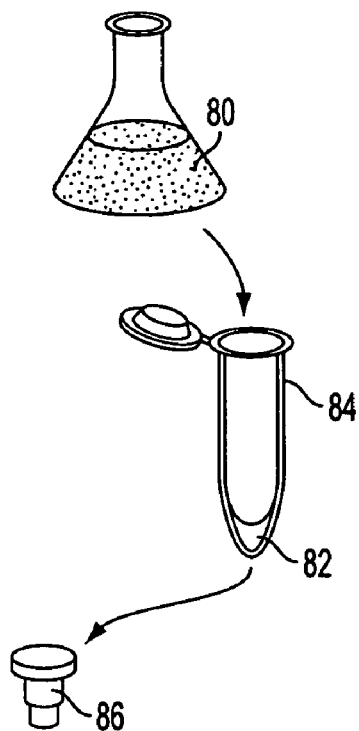
FIGS. 8, 9 and 10 illustrate a method of the present invention.
Figure 9:
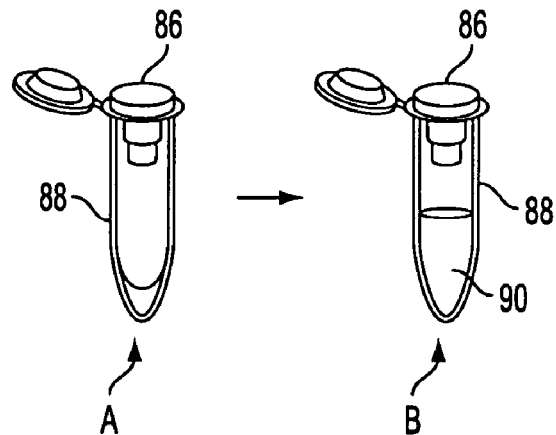
Figure 10:
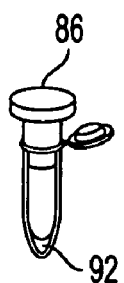

FIGS. 8-10 represent a flow diagram illustrating isolation of nucleic acids such as DNA or RNA from a biological material 80 using a filter column 86 of the present invention. FIG. 8 represents the first step of placing a lysate 82 of biological material 80 in a collection tube 84. This lysate 82 is spun to remove large lytic debris, and the "cleared" lysate is then applied to the top of a filter column 86 of the present invention.

Alternatively, the nucleic acid containing solution does not have to come directly from lysis of biological materials. This method can also purify nucleic acids following nucleic acid amplification, enzymatic restriction digestion, ligation, extension and virtually any solution containing significant nucleic acids.

Where small amounts of nucleic acid solutions are used, it is desirable to pre-wet the filter column with binding buffer before applying the nucleic acid solution. Alternatively, or additionally, the solution containing nucleic acid is transferred to the filter (wherein the nucleic acid material binds to the filter). This transfer may be performed at a first speed or rate employing any method known to one skilled in the art such as centrifugation or via vacuum. This binding step also includes a second step, which is performed at a high speed or rate of centrifugation, for example. Hence, solution is transferred from the filter column at a first speed followed by a second speed wherein the first speed is slower than the second speed. In one variation in which centrifugation is employed, the first slow speed is approximately 500 g or less, 1000 g or less, 1500 g or less, or 2000 g or less. This first step at a slow speed advantageously increases the resident time that the solution containing the nucleic acid material is in contact with the filter. The second relatively fast speed is approximately 10,000 g or more.

FIG. 9A illustrates the solution passing though a filter of the filter column 86 after centrifugation, during which the nucleic acids bind to the filter. The flow-through solution (from which the nucleotides have been mostly extracted) is retained at the bottom of a collection tube 88. Generally, tubes 88, 84 are discarded after use. Upon removal of the filter column 86 from the tube 88, the binding buffer (flow through) is discarded, and the filter column is replaced in a collection vessel (either a new tube or the same tube). FIG. 9B represents repeated washing of the filter column 86 with a washing buffer and centrifuging after each addition of washing solution into the top of the filter column. Once again the flow-through accumulated at the bottom of the tube 88 is discarded. FIG. 10 represents the last step of transferring the filter column 86 of the present invention into a smaller 0.5 mL tube 92 and the addition of a small volume of elution buffer into the filter column 86. Elution buffer is added to the filter in an amount substantially equal to the wetting capacity of the filter. Additional elution buffer may also be added to ensure that filter is not under-wetted. In one variation, additional elution buffer is added to the filter column in an amount that is between zero and approximately fifty percent of the wetting capacity of the filter. Alternatively, additional elution volume is added in an amount that is between zero and approximately 66% of the wetting capacity of the filter. In another variation, a volume of elution buffer is added to the filter column in an amount substantially equal to the volume defined by the shape of the filter. The volume defined by the shape of the filter includes the space occupied by both the void and solid filter fibers in a space circumscribed by the outermost fibers of the filter or approximately the volume of fluid that can occupy the space bounded by the bottom surface of the filter, the top surface of the filter, and the edges of the filter and/or the filter column walls. As a result of the addition of the elution buffer, the nucleic acids release from the filter into the elution buffer, which is centrifuged into the bottom of the 0.5 mL tube 92. When small volumes of elution buffer (e.g., 20 microliters or less) are used, the step of eluting the material is performed in two parts. First, the elution step is performed at a low-speed followed by a second step having a slow speed relative to the first slow-speed step. The elution step may be performed employing any method known to one skilled in the art including centrifugation or via vacuum. Hence, nucleic acid material is eluted from the filter column at a first speed followed by a second speed wherein the first speed is slower than the second speed. If centrifugation is employed, the first slow speed is approximately 500 g or less, 1000 g or less, 1500 g or less, or 2000 g or less. The first slow-speed step advantageously ensures that the filter is completely bathed in the elution buffer. A second spin at a higher speed (relative to the first spin) of approximately 10,000 g or more is done to allow collection of the maximum amount of elution buffer.

As shown in FIGS. 8-10, the inventive filter column permits use of more than one collection tube. All of the centrifugation steps can take place in a standard bench-top microcentrifuge (for example, Eppendorf 5415C), usually at accelerations less than 20,000 g.

Figure 11:
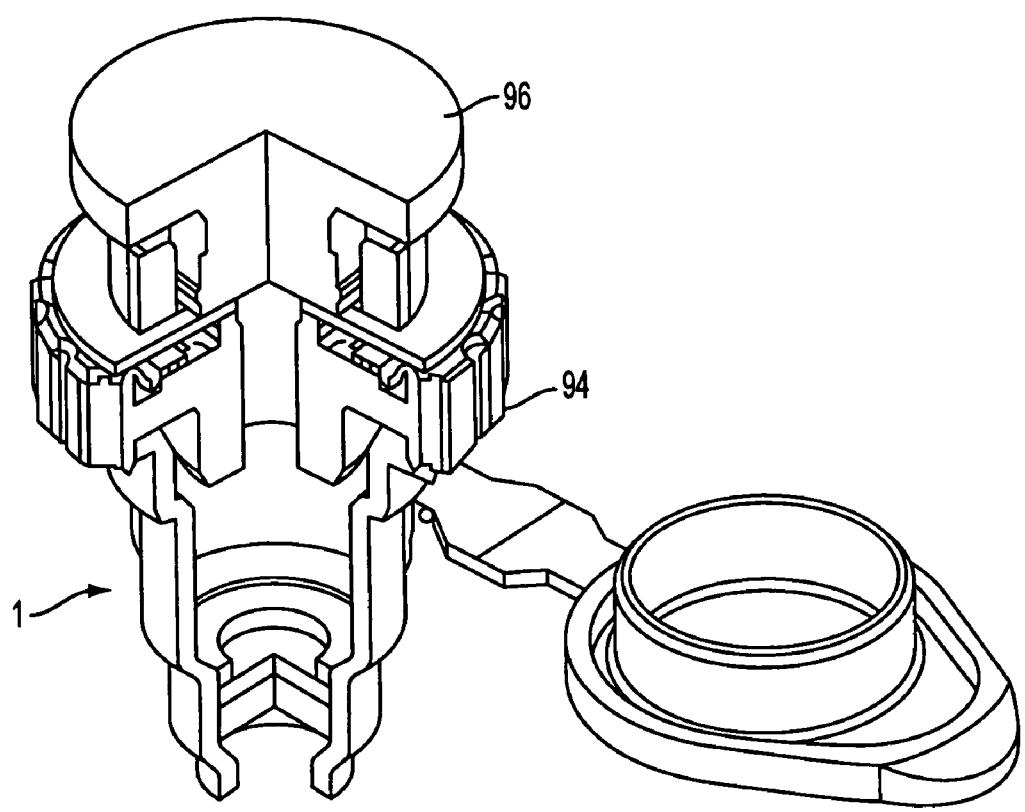
FIG. 11 illustrates a filter column of the present invention for use with a carrier device.

The biological material used with the filter column may also be provided by laser capture microdissection extraction device as described in U.S. patent application Ser. No. 09/844,187, entitled "LASER CAPTURE MICRODISSECTION (LCM) EXTRACTION DEVICE AND DEVICE CARRIER, AND METHOD FOR POST-LCM FLUID PROCESSING," the entirety of which is hereby incorporated by reference. As shown in FIG. 11, a filter column 1 attached to a LCM extraction device flange interface 94 which seats a laser capture microdissection extraction device 96. The biological material will be located on a bottom surface of the extraction device 96.

While the present invention has been described with reference to one or more particular variations, those skilled in the art will recognize that many changes may be made thereto without departing from the spirit and scope of the present invention. Each of these embodiments and obvious various thereof are contemplated as falling within the spirit and scope of the claimed invention, which is set forth in the claims.

What is claimed is:

1. A filter column 1, comprising:
a body having a passageway extending through the body; the body having a first end, a second end, an outer surface and an inner surface;
a filter located in the passageway;
a lid for closing one end of the passageway; and
at least one vent located in the lid, wherein the vent(s) is tapered.

2. The filter column of claim 1 wherein the vent(s) is tapered such that the vent is narrower towards the top of the lid.

3. The filter column of claim 1 wherein the vent(s) prevents fluid from being pushed through the filter when the lid is closed down onto the column.

4. The filter column of claim 1 wherein the vent(s) prevents fluid from escaping from around or through the lid.

5. The filter column of claim 1 wherein the vent(s) prevents fluid from being pushed through the filter when the lid is closed down onto the column and prevents fluid from escaping from around or through the lid.

6. A filter column comprising:
a body having a passageway extending through the body; the body having a first end, a second end, an outer surface and an inner surface;
a filter located in the passageway;
a lid for closing one end of the passageway;
at least one vent located in the lid; and at least one bearing surface on an outer surface for seating on at least one collection tube.

7. The filter column of claim 6 where the outer surface further includes a second bearing surface for seating on at least a second collection tube that has a different volume from the at least one collection tube.

8. The filter column of claim 6 further including at least a first body portion and a second body portion; wherein the cross-sectional area of the passageway at the first body portion is greater than the cross-sectional area of the passageway at the second body portion.

9. The filter column of claim 8 wherein the filter is located in the second body portion.

10. The filter column of claim 1 wherein the lid is connected to the body with a hinge.

11. The filter column of claim 1 wherein the vent(s) includes a curved surface.

* * * * *

UNITED STATES PATENT AND TRADEMARK OFFICE
CERTIFICATE OF CORRECTION

PATENT NO. : 7,556,733 B2
APPLICATION NO. : 11/076272
DATED : July 7, 2009
INVENTOR(S) : Thomas L. Smith et al.

It is certified that error appears in the above-identified patent and that said Letters Patent is hereby corrected as shown below:

In Claim 1, after "column" delete "1".

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,556,733 B2 |
| APPLICATION NO. | : 11/076272 |
| DATED | : July 7, 2009 |
| INVENTOR(S) | : Thomas L. Smith et al. |

It is certified that error appears in the above-identified patent and that said Letters Patent is hereby corrected as shown below:

Column 17, line 2, in Claim 1, after "column" delete "1".

This certificate supersedes the Certificate of Correction issued November 24, 2009.

Signed and Sealed this

Fifteenth Day of December, 2009

David J. Kappos
*Director of the United States Patent and Trademark Office*